United States Patent [19]
Cappello et al.

[11] Patent Number: 5,235,041
[45] Date of Patent: Aug. 10, 1993

[54] PURIFICATION OF STRUCTURALLY ORDERED RECOMBINANT PROTEIN POLYMERS

[75] Inventors: Joseph Cappello, San Diego; Franco A. Ferrari, La Jolla; Tina L. Buerkle, Solano Beach; Garret Textor, San Diego, all of Calif.

[73] Assignee: Protein Polymer Technologies, Inc., San Diego, Calif.

[21] Appl. No.: 869,212

[22] Filed: Apr. 13, 1992

Related U.S. Application Data

[63] Continuation of Ser. No. 635,463, Dec. 28, 1990, abandoned.

[51] Int. Cl.$^5$ ................................................. C07K 3/12
[52] U.S. Cl. ..................................... 530/353; 530/418; 530/420; 530/422; 530/423
[58] Field of Search ............... 530/353, 354, 355, 356, 530/357, 370, 412, 418, 420, 427, 422, 423

[56] References Cited

U.S. PATENT DOCUMENTS

| | | | |
|---|---|---|---|
| 4,511,502 | 4/1985 | Builder et al. | 530/344 |
| 4,512,922 | 4/1985 | Jones et al. | 424/85.8 |
| 4,518,526 | 5/1985 | Olson | 530/344 |
| 4,620,948 | 11/1986 | Builder et al. | 530/419 |
| 4,652,630 | 3/1982 | Bentle et al. | 530/344 |
| 4,766,205 | 8/1988 | Ghosh-Dashidar | 530/412 |

FOREIGN PATENT DOCUMENTS 8704726 8/1987 PCT Int'l Appl. .

OTHER PUBLICATIONS

Marston, Biochem. J., 240, pp. 1–12 (1986).
Kane et al., Trend-Biotech., vol. 6, pp. 95–101 (1988).
Marston et al., Biotechnology, vol. 2 pp. 799–804 (1984).

*Primary Examiner*—Jeffrey E. Russel
*Attorney, Agent, or Firm*—Bertram I. Rowland

[57] ABSTRACT

Recombinant structural and functional polymers are purified by lysing of the cellular host, separation of the solid materials, washing and extraction of contaminants using a detergent solution at elevated temperatures.

6 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
      ( A ) LENGTH: 26 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:1:

Tyr Thr Ile Thr Val Tyr Ala Val Thr Gly Arg Gly Asp Ser Pro Ala
 1               5                  10                 15

Ser Ser Lys Pro Ile Ser Ile Asn Tyr Cys

PURIFICATION OF STRUCTURALLY ORDERED RECOMBINANT PROTEIN POLYMERS

This is a continuation of application Ser. No. 07/635,463, filed Dec. 28, 1990, now abandoned.

INTRODUCTION

1. Technical Field

The field of this invention is the purification of proteins from recombinant host cells.

2. Background

With the advent of recombinant technology, numerous new products became available. For the first time, one could now prepare complicated proteins in commercially useful amounts. Among the proteins of interest are structural proteins, where the proteins are characterized by having a relatively small repeating unit. The structural proteins are found in a wide variety of contexts, being present as collagen, keratin, elastin, silk, mollusc adhesive proteins, and the like. The opportunity to make these proteins, by recombinant technology offers the opportunity to modify their physical characteristics, so that one can produce a variety of proteins which will differ from the characteristics of the natural protein. Thus, one can enhance tensile strength, elasticity, feel, viscosity, binding properties, response to water, response to changes in temperature, introduce functional groups and the like.

For the most part, the polymers with the small repeating units have a high molecular organization which results in low solubility in conventional solvents. When the proteins are prepared by recombinant techniques they are normally produced within the microorganism in soluble or insoluble form. Upon lysis of the microorganism and recovery of the protein, the recombinant protein may be an insoluble aggregate. These insoluble aggregates may incorporate various proteins and other matter present in the cytoplasm of the organism.

Many of the applications for the proteins will require a product of substantial purity. Particularly, where the proteins may find use, by themselves or in combination with other materials, for applications in the medical field, such as sutures, prosthetic devices, gauze, dressings, vascular vessel substitutes, or the like, the proteins must be free of contaminants which will affect their physiological properties and acceptance by the host. In other situations, contaminants must be removed which might deleteriously affect the characteristics of the protein product.

There is, therefore, substantial interest in finding techniques which provide for purification of the structural and functional polymers without significant degradation or deterioration of the protein products with loss of desirable properties, as well as providing an economically efficient process as to materials employed, equipment employed and the number of steps.

3. Relevant Literature

United States patents directed to purification of recombinant proteins include, U.S. Pat. Nos. 4,518,526; 4,652,630; 4,511,502; 4,512,922; and 4,620,948. See also WO87/04726.

Articles of interest include Marston et al., Biotechnology (1984) 2:799-804; Marston, Biochem. J. (1986) 240:1-12; and Kane and Hartley, Trends in Biotechnology (1988) 6:95-101.

SUMMARY OF THE INVENTION

Methods for purification of recombinantly produced structural and functional polymers are provided. Harvested cells are treated to promote insoluble protein product, followed by lysis under conditions resulting in aggregation and/or precipitation of the protein product. After isolation of the insoluble protein product, contaminants are extracted from the protein solids at an elevated temperature leaving a substantially purified product. The extraction step may be repeated with the same or different extractant to provide a higher level of purity.

DESCRIPTION OF THE SPECIFIC EMBODIMENTS

Methods are provided for the purification of substantially insoluble recombinantly prepared structural or functional polymers The polymers are characterized by having a high degree of internal structural order as a result of extended stretches of small repeating units, which provide for substantial alignment of stretches of the repeating units, strong hydrogen bonding, and desirable physical properties, such as high tensile strength.

Generally, the process comprises an initial step of treating the cells containing the expressed product to insolubilize the protein product, e.g. by heating or cooling. The cells are then lysed in a buffer resulting in aggregation and/or precipitation, where the buffer may contain agents which aid in the separation. The protein produced is separated from other components of the lysate and then extracted to remove contaminants while remaining insoluble. The extraction process may be repeated with the same or different extracting medium as appropriate. One or more washings may be employed after each extraction. A substantially purified product is obtained without significant physical or chemical modification, providing a product having the desired properties.

The polymers of interest in the subject invention may be any of a wide variety of structural protein polymers having long stretches of repeating units, where repeating units will generally be of from about 3-20, more usually 3-14 amino acids, particularly 3-9 amino acids. The proteins include individually or in combination, members of the collagen family, keratin, elastin, fibronectin, silks, laminin and other fibrous proteins. Other structural proteins include the protein or glycoprotein elements of thick, intermediate or thin filaments in higher organisms, the annelid or anthropod, bacterial flagellin, resilin, troponin C, tropomyosin, eucaryotic egg shell proteins, insect cuticle proteins and architectural proteins involved with eucaryotic developmental processes such as tissue organization, as well as specialty proteins, such as mollusc adhesive protein. The polymers may provide for homopolyaers, block co-polymers, alternating co-polymers, polymers having intervening groups, combinations of repeating units from different structural polymers forming a single unit, and the like. Thus, the characteristics of the polymers may vary widely but will uniformly be substantially insoluble in conventional solvents, particularly in water at above 80° C., usually not more than about 100° C., more usually about 90° C.

The subject polymers may be prepared in a wide variety of microorganisms, both prokaryotic and eukaryotic. For the most part, the organisms will be prokaryotic, such as E. coli, B. subtilis, B. stearothermophilus, Streptomyces, etc. In some instances eukaryotic organisms may be employed, such as yeast, filamentous fungi, etc. The organisms which will be used will be transformed with the appropriate DNA, which may provide for integration into the genome of the host cell or for stable episomal elements which may be of high or low copy number, preferably above about 5.

The cells are grown in an appropriate nutrient medium to high density, where the subject protein will be at least about 1% of total cell protein, more usually at least about 5% of total cell protein.

Usually, the cells will be grown to high density, generally of at least about 5 g/L usually at least about 20 g/L, preferably at least about 30 g/L dry weight or higher. Depending upon the particular construct which has been employed for expression of the subject proteins, one may have constitutive or inducible expression of the product. In the case of constitutive expression, the product will be continuously formed as the cells grow. By contrast, for inducible expression, one may provide for induction when the cells reach a predetermined cell density. A large number of constitutive and inducible promoters are available, which provide for the desired level of expression. Strong promoters which may be used include lambda $P_R$ and $P_L$, $T_7$ gene 10, alkaline phosphatase, tac, pho, trp, lac, spoVG, aprE, α-amylase, etc.

The growth medium which is employed is not critical, any conventional medium may be used. Illustrative media include LB, complex media containing organic nitrogen sources, such as yeast extract, or minimal or defined media.

When the desired product level has been achieved, production may be stopped in a variety of ways. Desirably, the plasmid will be inactivated at the end of the fermentation run. Inactivation and providing the protein product in an insoluble form may be achieved concurrently. Physical e.g. mechanical or thermal, or chemical treatments may be employed. Treatments employed may include freezing ($\leq 0°$ C.), heating, usually between about 60°-80° C., hydrodynamic shearing, drying or precipitation by addition of acid, base, salts or organic solvents. Chemical inactivation may be achieved with compounds such as quaternary amines, e.g. dodecyl dimethyl ammonium chloride, sodium azide, or the like. Lysing of the cells may also be achieved by appropriate selection of the conditions or the different events may be achieved individually.

Illustrative of one approach, after inactivation of the plasmid by heating, the cells are then harvested to separate the cells from the fermentation broth. Various techniques may be used for harvesting, desirably using centrifugation, generally at 2,500 to 10,000 xg, more usually 4,000 to 8,000 xg. Usually, the cells may be harvested after about 30 min of centrifugation to provide compaction of the cells. The supernatant may then be discarded and the residue washed with an appropriate buffered aqueous medium to remove any residual fermentation medium components. Typically the buffered medium will be at a temperature in the range of about 1°-10° C., usually at about 4° C. The cellular residue is dispersed in the aqueous medium to ensure the substantial dilution and removal of the fermentation medium components. Various buffers may be used, such as Tris, phosphate, Hepes, Mops, etc., where the pH will generally be in the range of from about 7 to 9, preferably about 8. Usually, the wash volume will be at least equal to the residue volume, usually being in the range of from about 2 to 5 times the residue volume. The residue comprising the cellular components is then separated again, conveniently by centrifugation as described above and the residue is then ready for lysis or storage. For storage, the residue may be frozen at about $-20°$ C. (20–30 h). To prepare the frozen residue for lysis, the residue is thawed, usually at 1°–10° C., more usually 4° C., usually requiring at least about 10 h, and up to 20 h, before addition of the buffered medium. Other thawing protocols may also find use.

The cells may be lysed by any convenient means, such as freezing, mechanically, enzymatic, e.g. lysozyme or the like. A convenient method is to use a Manton-Gaulin Press at at least about 5,000 psi and not more than about 15,000 psi usually in the range of about 7,500 to 10,000 psi. The cellular material is suspended in an appropriate aqueous medium, such as the media described for the wash buffer. The suspending solution will generally be at least equal to the weight of cellular material and generally at least 2 times, and not more than 10 times the weight of cellular material, usually from about 3–4 times the weight of cellular material. Usually, the suspension will be passed through the press more than once, usually not more than about 5 times, preferably about 3 times, to achieve disruption of at least 90%, usually 95%, more usually 99% of the total number of cells.

The resulting dispersion of disrupted cells in the medium is then separated so as to form a substantially solid concentrated fraction and a liquid fraction. Conveniently, this may be achieved by centrifugation for at least 3 min, although longer times may be employed. The resulting supernatant containing soluble proteins and other contaminants is discarded, leaving a solid residue comprising a major portion of the generated product and solid contaminants.

The residue is then extracted by suspension of the residue in a solution of an appropriate solubilizing agent, more particularly a surfactant, e.g. an anionic detergent, particularly a sulfuric acid based salt, more particularly sodium dodecylsulfate (SDS). The surfactant will be in the range of about 1–5%, preferably about 2% (w/v). The amount of solution employed will be at least twice the weight of the solids, generally ranging from about 4 to 20 times, more usually from about 4 to 10 times the solids weight.

The suspension is heated to at least about 60° C., usually to at least about 75° C. and less than about 100° C., preferably in the range of about 80 to 90° C. for at least about 15 min, more usually at least about 30 min, usually not more than about 180 min, preferably not more than about 120 min. The mixture is agitated during the heating. After the heating, the solid portion is then separated from the liquid portion, conveniently by centrifugation at at least about 5,000 xg and not more than about 15,000 xg, usually in the range of about 6,000 to 10,000 xg, for sufficient time for compaction of the solids. Generally, the centrifugation will be carried out for at least about 10 min and not more than about 60 min, generally from about 15 to 30 min, and the supernatant discarded. The purity of the recovered solids may then be determined by any convenient method, e.g. amino acid composition. If a higher purity is desired, another extraction treatment may be performed under the same conditions as previously or different conditions, frequently milder conditions. For example, where the first extraction used 2% surfactant, the second extraction may use 1–1.5% of an analogous surfactant. To remove any of the solubilizing agent, the product may be washed or diafiltered.

For washes, the solids are suspended in water, where the water will be at least about twice, usually in the range of 5 to 20, more usually in the range of 8 to 12 times the weight of solids. The temperature will generally be in the range of about 60° to 95° C., usually 70° to 90° C. The slurry is agitated for from about 15 to 75 min and the solids isolated, e.g. by centrifugation.

The product may then be dried by any convenient means, such as freeze drying, spray drying, or the like. The product is then ready for use as appropriate.

The following examples are offered by way of illustration and not by way of limitation.

EXPERIMENTAL

A number of polymers were prepared as described in PCT/US/87/02822, filed Oct. 29, 1987 and PCT/US89/05016, filed Nov. 7, 1989. The following table indicates the polymers prepared and their characteristics.

TABLE 1

| Polymers* | Plasmid  | M.W.   | Amino Acids |
|-----------|----------|--------|-------------|
| SLP-3     | pSY 1186 | 83,000 | 1178        |
| SLP4      | pSY 1398 | 76,000 | 1101        |
| SLP3-F    | pPT 0101 | 72,700 | 980         |
| SLP3-C    | pPT 0105 | 97,100 | 1333        |

*SLP-silk like polymer having repeating unit of silk fibroin.
SLP3-F - SLP3 backbone with fibronectin cell binding domain incorporated.
SLP3-C - SLP3 backbone with cross-linking oligopeptide domain incorporated.

The strain employed was *E. coli* HB101:F-, hsd S20, (rB-, mB-), recA13, ara−14, proA−2, lacY1, galK2, rpsL20, (smR), xyl−5, mtl−1, supE44, thil, leuB6, lambda-. (ATCC Catalog No. 33694)

FERMENTATION CONDITIONS

The fermentor used was a 15 liter Chemap with a 10 liter working volume or a 1500 liter Chemap with a 1000 liter working volume. The culture conditions were: temperature=30° C., pH=6.8; NH$_4$OH (30% v/v) was used for pH regulation. The headspace pressure was below 0.3 bar. The dissolved oxygen was regulated at 50%. The air flow varied from 0.5 liters/min to 20 liters/min. The agitation rate varied between 200 and 1500 rpm for the smaller scale fermentor and 100 and 500 rpm for the larger scale fermentor.

For the smaller scale fermentations, the fermentor was inoculated with a 5% (v/v) inoculum grown in medium A (Table 2) for 15 hours at 30° C. under agitation. Medium B (Table 2) was the fermentor medium. The starting volume was 5 liters.

For the larger scale fermentations, a series of inoculums were prepared. First, a 20 liter fermentor containing 7 liters of medium A (Table 2) was inoculated with a 5% inoculum grown in medium A (Table 2) for 15 hours at 30° C. under agitation. Culture conditions were as described above. The fermentation was allowed to proceed for 16 to 18 hours. Second, a 150 liter fermentor containing 70 liters of medium A (Table 2) was inoculated with the broth from the 20 liter fermentor. Culture conditions were as described above. The fermentation was allowed to proceed for 12 hours. The final 1500 liter fermentor containing 700 liters of medium B (Table 2) was inoculated with the broth from the 150 liter fermentor.

Periodically throughout the final fermentations, a concentrated solution (5 x) of medium B was added to the fermentor in order to prevent the carbon and nitrogen concentrations from becoming limiting to the growth of the cell. When the culture reached an OD$_{600}$ of approximately 60.0, the temperature was increased to 42° C. for 30 min, then lowered to 40° C. for 3 hours. The cells were then harvested by centrifugation and frozen at either −20° C. or −70° C. until processed.

TABLE 2

| Constituent              | g/L                |
|--------------------------|--------------------|
| Medium A; LB Medium      |                    |
| NaCl                     | 10                 |
| tryptone                 | 10                 |
| yeast extract            | 5                  |
| kanamycin                | $5 \times 10^{-3}$ |
| Medium B                 |                    |
| (NH$_4$)SO$_4$           | 5.6                |
| K$_2$HPO$_4$             | 6.7                |
| MgSO$_4$.7H$_2$O         | 7.8                |
| NaH$_2$PO$_4$.H$_2$O     | 3.8                |
| EDTA                     | 0.98               |
| Trace Elements           | 1 ml               |
| yeast extract or NZ Amine| 50                 |
| glycerol                 | 20                 |
| kanamycin                | $5 \times 10^{-3}$ |

PERCENT SOLIDS DETERMINATION

The tare weight of a 30×100 mm centrifuge tube was determined. 30 mls of disrupted cell suspension were then placed into the tube, which was subsequently centrifuged at 16,000 rpm in a Sorval RC5B centrifuge with a SS34 rotor for 30 minutes. The supernatant solution was then decanted. Percent solids (w/v) was determined according to the following formula: (net weight of pellet/30 mls)×100.

ANTIBODY PRODUCTION AND PROTEIN ANALYSIS PROCEDURES

Preparation of Antibody to Artificially Synthesized Peptides

Synthetic peptide of sequence (GAGAGS)$_8$GAAGY was coupled to BSA using the glutaraldehyde procedure of Kagen and Glick (1979) infra. The degree of coupling was monitored using trace amounts of radioactive iodinated synthetic peptide. Peptide conjugates at a concentration of 1 mg/ml in complete Freund's adjuvant were used to immunize rabbits at day 0. Animals were re-injected with antigen in Freund's incomplete adjuvant at day 30 and titered at day 60. Positive sera was detected using a microtiter RIA using the synthetic peptide as antigen. Kagen and Glick (1979), in Methods of Radioimmunoassay, Jaffe and Berman (eds.), Academic Press, p. 328.

Following the procedure described above an additional peptide was synthesized having the formula "Tyr-Thr-Ile-Thr-Val-Tyr-Ala-Val-Thr-Gly-Arg-Gly-Asp-Ser-Fro-Ala-Ser-Ser-Lys-Pro-Ile-Ser-Ile-Asn-Tyr-Cys" of fibronectin (SEQ ID NO: 1) (the cell binding portion). This was coupled to keyhole limpet hemocyanin for use as an immunogen. Polyclonal antisera was then prepared as described above which bound to the cell binding peptide.

Determination of Polymer Concentration by Dot Blot Analysis

Sample Dilutions

100 μl of 4.5 M LiClO$_4$ were added to each of the top wells of a microwell plate (Nunc).

3 μg of the appropriate purified protein polymer standard in 25 μl of 2x Sample Buffer (0.0625 M Tris base, pH 6.8, 2% SDS, 10% glycerol, 0.001% Bromophenol Blue, 5% β-Mercaptoethanol) were added to the first well. Aliquots corresponding to 30 μg of protein from the unknown samples to be analyzed in 25 μl of 2x Sample Buffer, were added to the other top wells. A volume of distilled water was added to bring the final volume to 300 μl. 150 μl of buffer A (50 μM Tris, 10 μM EDTA, pH 7.0) were added to all remaining wells. Using a multichannel pipettor (Costar) 150 μl of the top wells were serially diluted.

Blot Preparation

Nitrocellulose paper (Sartorius, SM11307) and Whatman filters were soaked in 1x TSA solution (50 mM Tris-HCl, pH 7.4, 0.9% NaCl, 0.2% Sodium azide) for approximately 30 s. They were applied to the dot blot apparatus (Schleicher & Schull). The apparatus was clamped down and vacuum was applied. Using a multichannel pipettor, 100 μl of the previous dilutions were loaded to each well.

After samples were loaded, the nitrocellulose paper was soaked in Blotto (5% non-fat dry milk, 50 mM Tris-HCl, pH 7.4, 0.9% NaCl, 0.2% Sodium Azide) for approximately 10 minutes. The nitrocellulose was then incubated in an antibody solution, at 1:1000 dilution of peptide specific antisera in Blotto, for at least 16 hours at room temperature or 2 hours at 37° C. under gentle shaking. The nitrocellulose was then washed 5 times with 1x TSA for 15 minutes each.

The blot was then placed in 15 ml of Blotto containing $0.5 \times 10^7$ cpm of $^{125}$I-protein A and gently agitated for 2 hours at room temperature. The filter was washed for 2 hours with a minimum of 5 changes of TSA, rinsed once with deionized water and air dried. The blot was covered with Saran wrap and autoradiographed.

Protein Concentration Determination

Total protein concentrations were determined by the Lowry method. (Lowry et al., 1951, J. Biol. Chem).

Amino Acid Analysis

Amino acid compositions were determined by the PTC derivitization procedure of Henrickson and Meredith (1984). Protein samples were hydrolyzed with 5.7 N constant boiling HCl at 108° C. for 24 hours in vacuo. After reaction with PITC, amino acid derivatives were detected at 254 nm by HP$_L$C reverse phase chromatography using a Waters system and a Supelco C18 column (4.6 nm × 25 cm) with a linear gradient of 0-50% acetonitrile in 0.1 M NH$_4$OAc, pH 6.78, as a mobile base. Henrickson, R.L. and Meredith, S. C. (1984) Amino Analysis by Reverse Phase High Performance Liquid Chromatography. *Anal. Biochem.*, 137:65-74.

EXAMPLES

Unless otherwise stated, the temperature of the centrifuges, for all centrifugation steps, was maintained at 18°-22° C. Unless otherwise stated, all procedures were performed and all materials were used at room temperature. Unless stated as a plateau, the centrifugation times indicate the time from machine activation, rotor acceleration, to power shut off (it does not include the time for rotor deceleration). A centrifugation plateau is defined as the period of time that the centrifugation occurs at constant speed (it excludes acceleration and deceleration times). Unless otherwise stated, the water used was deionized water.

Example 1

The protein polymer, SLP3, was recovered and purified from 250 grams of frozen cell paste of *E. coli* strain PSY1186 (HB101 containing the gene encoding SLP3). The cell paste was thawed for 15 hours at 4° C. and then was suspended to a volume of 1 liter with 50 mM sodium phosphate buffer, pH=7.0. The suspension was subjected to cellular disruption using a Manton-Gaulin (MG15) press at 8000 psi for 3 successive passes. The cell lysate suspension had a solids content of 21%. The cell lysate was centrifuged for 20 minutes at 10,000 rpm in a GSA rotor using a Sorvall RC5B centrifuge (centrifugal force = 16,318 × gravity). The cell lysate supernatant was removed and discarded.

The cell lysate pellet was resuspended to a volume of 0.9 liter with water. The suspension was homogenized until a homogeneous slurry was obtained. 100 ml of a 20% (w/v) solution of sodium dodecyl sulphate (SDS) (technical grade, Sigma) was added while mixing in order to achieve a final SDS concentration of 2.0% (w/v). The suspension was heated to approximately 90° C. with stirring in a water bath maintained at about 95° C. for 70 minutes. This SDS (#1) suspension was centrifuged for 20 minutes at 7,500 rpm in a GSA rotor using a Sorvall RC5B centrifuge (centrifugal force = 9,179 × gravity). The SDS (#1) supernatant was removed and discarded.

The SDS (#1) pellet was resuspended to a volume of 0.95 liter with water. The suspension was homogenized until a homogeneous slurry was obtained. 50 ml of a 20% (w/v) solution of SDS (technical grade, Sigma) was added while mixing in order to achieve a final SDS concentration of 1.0% (w/v). The suspension was heated to approximately 90° C. with stirring in a water bath maintained at about 95° C. for 68 minutes. This SDS (#2) suspension was centrifuged for 20 minutes at 7,500 rpm in a GSA rotor using a Sorvall RC5B centrifuge (centrifugal force = 9,179 × gravity). The SDS (#2) supernatant was removed and discarded The SDS (#2) pellet was resuspended to a volume of 1 liter with water. The suspension was homogenized until a homogeneous slurry was obtained. The suspension was heated to approximately 80° C. with stirring in a water bath maintained at about 85° C. for 20 minutes. This water wash (#1) suspension was centrifuged for 20 minutes at 7,500 rpm in a GSA rotor using a Sorvall RC5B centrifuge (centrifugal force = 9,179 × gravity) The water wash (#1) supernatant was removed and discarded The water wash (#1) pellet was resuspended to a volume of 0.75 liter with water. The suspension was homogenized until a homogeneous slurry was obtained. The suspension was heated to approximately 84° C. with stirring in a water bath maintained at about 88° C. for 27 minutes. This water wash (#2) suspension was centrifuged for 20 minutes at 7,500 rpm in a GSA rotor using a Sorvall RC5B centrifuge (centrifugal force = 9,179 × gravity). The water wash (#2) supernatant was removed and discarded.

The water wash (#2) pellet was resuspended to a volume of 625 ml with water and homogenized. The sample was shell frozen in glass lyophilization flasks at −40° C. by immersion in a dry ice isopropyl alcohol bath. The sample was lyophilized to a dry, white powder using a Virtis Freezemobile 25 SL for approximately 66 hours.

The protein concentration in both the supernatants and pellets was determined after each centrifugation step using the Lowry method. The polymer product concentration in both the supernatants and the pellets after each centrifugation step was determined immunologically by dot blot analysis. The final dried product was analyzed by amino acid composition in order to determine the protein purity (ratio of protein polymer product to total protein) and the absolute purity (ratio of protein polymer product to total dry weight). Results were as shown in Table 3.

Example 2

The protein polymer, SLP3, was recovered and purified from 125 grams of freshly harvested (unfrozen) cell paste of *E. coli* strain PSY1186 (HB101 containing the gene encoding SLP3). The cell paste was suspended to a volume of 500 mls with 50 mM Tris buffer, pH=8.0. The suspension was subjected to cellular disruption using a Manton-Gaulin (MG15) press at 8000 psi for 3 successive passes. The cell lysate was centrifuged for a 3 minute plateau at 5,000 rpm in a GSA rotor using a Sorvall RC5B centrifuge (centrifugal force=4,080×gravity) at 4° C. The cell lysate supernatant was removed and discarded.

The cell lysate pellet was resuspended to a volume of 0.45 liter with water. The suspension was homogenized until a homogeneous slurry was obtained. 50 ml of a 20% (w/v) solution of sodium dodecyl sulphate (SDS) (technical grade, Sigma) was added while mixing in order to achieve a final SDS concentration of 2.0% (w/v). The suspension was heated to approximately 92° C. with stirring in a water bath maintained at about 95° C. for 40 minutes. This SDS (#1) suspension was centrifuged for 20 minutes at 7,500 rpm in a GSA rotor using a Sorvall RC5B centrifuge (centrifugal force=9,179×gravity) at 4° C. The SDS (#1) supernatant was removed and discarded. The total protein and polymer product concentrations in both the supernatants and pellets were determined after each centrifugation step, by Lowry and immunological dot blot analyses, respectively. The protein purity of the final pellet was determined by amino acid composition. Results were as shown in Table 3.

Example 3

The protein polymer, SLP4, was recovered and purified from 535 liters of frozen cell slurry of *E. coli* strain PSY1398 (HB101 containing the gene encoding SLP4). The cell paste was thawed to room temperature for 15 hours. The suspension was processed in two approximately equal batches. The suspension was subjected to cellular disruption using a Manton-Gaulin (MG3) press at 7500 psi for 3 successive passes. The temperature of the cell lysate was maintained between 8° and 20° C. using a heat exchanger. The cell lysate suspension had a solids content of 14% for the first batch and 11% for the second. 195 liters of 50 mM sodium phosphate buffer, pH=7.0 was added to the cell lysates and mixed. The cell lysate suspensions were centrifuged using continuous tubular bowl centrifuges (Sharples 322E-16Y) at 15,000 rpm (centrifugal force=7,000×gravity). The dimensions of the tubular bowl rotors were 10.5 cm in diameter by 60 cm in length. The feed rates were approximately 0.5 to 0.7 liters/minute. The cell lysate supernatants were discarded.

The cell lysate pellets from each batch were resuspended to 100 liters in water. Each batch suspension was stirred until a homogeneous slurry was obtained. The suspension from the first batch was added with mixing to 300 liters of a 2% (w/v) solution of sodium dodecyl sulphate (SDS) (technical grade, Sigma) which had been heated to 90° C. in order to achieve a final SDS concentration of 1.5% (w/v). The suspension was heated to approximately 90° C. with stirring using a steam jacket for 109 minutes. This SDS (#1A) suspension was centrifuged using continuous tubular bowl centrifuges (Sharples 322E-16Y) at 15,000 rpm (centrifugal force=7,000×gravity). The feed rates were approximately 0.5 to 0.7 liters/minute. The SDS (#1A) supernatant was removed and discarded.

The SDS (#1A) pellet was resuspended to a volume of 100 liters with water. The suspension was stirred until a homogeneous slurry was obtained. This suspension was added with mixing to 100 liters of a 2% (w/v) solution of sodium dodecyl sulphate (SDS) (technical grade, Sigma) in order to achieve a final SDS concentration of 1.0% (w/v). The suspension was heated to approximately 90° C. using a steam jacket for 71 minutes. This SDS (#2A) suspension was centrifuged using continuous tubular bowl centrifuges (Sharples 322E-16Y) at 15,000 rpm (centrifugal force=7,000×gravity). The feed rates were approximately 0.5 to 0.7 liters/minute. The SDS (#2A) supernatant was removed and discarded.

The SDS (#1B) pellet suspension from the second batch was added with mixing to 200 liters of a 2.25% (w/v) solution of sodium dodecyl sulphate (SDS) (technical grade, Sigma) in order to achieve a final SDS concentration of 1.5% (w/v). The suspension was heated to approximately 90° C. using a steam jacket for 68 minutes. This SDS (#1B) suspension was centrifuged using continuous tubular bowl centrifuges (Sharples 322E-16Y) at 15,000 rpm (centrifugal force=7,000×gravity). The feed rates were approximately 0.5 to 0.7 liters/minute. The SDS (#1B) supernatant was removed and discarded.

Both of the accumulated SDS pellets (#2A and #1B) were combined and resuspended in 30 liters of water. The pellet was homogenized until a homogeneous slurry was obtained. 50 liters of 100° C. water was added in order to achieve a temperature of 60° C. which was maintained for 30 minutes by immersion in a heated water bath. The combined SDS pellet suspension was then heated to approximately 82° C. with stirring in a water bath maintained at about 85° C. for 30 minutes. This water wash (#1) suspension was centrifuged for 40 minutes at 5,000 rpm in a H6000A rotor using a Sorvall RC3B centrifuge (centrifugal force=7,280×gravity). The water wash (#1) supernatant was removed and discarded.

The water wash (#1) pellet was resuspended to a volume of 200 liters with water. The suspension was homogenized until a homogeneous slurry was obtained. The suspension was heated to approximately 60° C. with stirring in a water bath maintained at about 85° C. for 30 minutes. This water wash (#2) suspension was centrifuged for 40 minutes at 5,000 rpm in a H6000A rotor using a Sorvall RC3B centrifuge (centrifugal force=7,280×gravity). The water wash (#2) supernatant was removed and discarded The water wash (#2) pellet was resuspended to a volume of 60 liters with water and homogenized. The sample was frozen and dried by lyophilization using a HULL 65272F100 lyophilizer. The dried sample was a dry, tan powder.

The protein concentration in both the supernatants and pellets was determined after each centrifugation step using the Lowry method. The polymer product concentration in both the supernatants and the pellets after each centrifugation step was determined immunologically by dot blot analysis. The final dried product was analyzed by amino acid composition in order to determine the protein purity (ratio of protein polymer product to total protein) and the absolute purity (ratio of protein polymer product to total dry weight). Results were as shown in Table 3.

Example 4

The protein polymer, SLP4, was recovered and purified from 150 grams of frozen cell slurry of E. coli strain PSY1398 (HB101 containing the gene encoding SLP4). The cell paste was thawed at room temperature and then was suspended to a volume of 0.5 liter with 50 mM sodium phosphate buffer, pH=7.0. The suspension was subjected to cellular disruption using a Manton-Gaulin (MG15) press at 8000 psi for 3 successive passes. The cell lysate suspension had a solids content of 10%. The cell lysate was centrifuged for 30 minutes at 12,000 rpm in a GSA rotor using a Sorvall RC5B centrifuge (centrifugal force=23,499×gravity). The cell lysate supernatant was removed and discarded.

The cell lysate pellet was resuspended to a volume of 0.56 liter with water. The suspension was homogenized until a homogeneous slurry was obtained 60 ml of a 20% (w/v) solution of sodium dodecyl sulphate (SDS) (technical grade, Sigma) was added while mixing in order to achieve a final SDS concentration of 2.0% (w/v). The suspension was heated to approximately 90° C. with stirring in a water bath maintained at about 99° C. for 70 minutes. This SDS (#1) suspension was centrifuged for 20 minutes at 7,500 rpm in a GSA rotor using a Sorvall RC5B centrifuge (centrifugal force=9,179×gravity). The SDS (#1) supernatant was removed and discarded The SDS (#1) pellet was resuspended to a volume of 0.475 liter with water. The suspension was homogenized until a homogeneous slurry was obtained. 25 ml of a 20% (w/v) solution of SDS (technical grade, Sigma) was added while mixing in order to achieve a final SDS concentration of 1.0% (w/v). The suspension was heated to approximately 90° C. with stirring in a water bath maintained at about 95° C. for 60 minutes. This SDS (#2) suspension was centrifuged for 20 minutes at 7,500 rpm in a GSA rotor using a Sorvall RC5B centrifuge (centrifugal force=9,179×gravity). The SDS (#2) supernatant was removed and discarded.

The SDS (#2) pellet was resuspended to a volume of 0.5 liter with water. The suspension was homogenized until a homogeneous slurry was obtained. The suspension was heated to approximately 82° C. with stirring in a water bath maintained at about 85° C. for 30 minutes. This water wash (#1) suspension was centrifuged for 20 minutes at 7,500 rpm in a GSA rotor using a Sorvall RC5B centrifuge (centrifugal force=9,179×gravity). The water wash (#1) supernatant was removed and discarded.

The water wash (#1) pellet was resuspended to a volume of 0.5 liter with water. The suspension was homogenized until a homogeneous slurry was obtained. The suspension was heated to approximately 80° C. with stirring in a water bath maintained at about 85° C. for 30 minutes. This water wash (#2) suspension was centrifuged for 20 minutes at 7,500 rpm in a GSA rotor using a Sorvall RC5B centrifuge (centrifugal force=9,179×gravity). The water wash (#2) supernatant was removed and discarded.

The water wash (#2) pellet was resuspended to a volume of 500 ml with water and homogenized. The sample was shell frozen in glass lyophilization flasks at −40° C. by immersion in a dry ice isopropyl alcohol bath. The sample was lyophilized to a dry, white powder using a Virtis Freezemobile 25 SL for approximately 66 hours.

The protein concentration in both the supernatants and pellets was determined after each centrifugation step using the Lowry method. The polymer product concentration in both the supernatants and the pellets after each centrifugation step was determined immunologically by dot blot analysis. The final dried product was analyzed by amino acid composition in order to determine the protein purity (ratio of protein polymer product to total protein). Results were as shown in Table 3.

Example 5

The protein polymer, SLP3-F, was recovered and purified from 125 grams of frozen cell paste of E. Coli strain PPT$_{0101}$ (HB101 containing the gene encoding SLP3-F). The cell paste was suspended to a volume of 500 mls with 50 mM Tris buffer, pH=8.0 and allowed to thaw to room temperature. The suspension was homogenized to yield a homogeneous cell suspension. The suspension was subjected to cellular disruption using a Manton-Gaulin (MG15) press at 8,000 psi for 3 successive passes. The cell lysate was centrifuged for a 3 minute plateau at 5,000 rpm in a GSA rotor using a Sorvall RC5B centrifuge (centrifugal force=4,080×gravity) at 4° C. The cell lysate supernatant was removed and discarded.

The cell lysate pellet was resuspended to a volume of 0.45 liter with water. The suspension was homogenized until a homogeneous slurry was obtained. 50 ml of a 20% (w/v) solution of sodium dodecyl sulphate (SDS) (technical grade, Sigma) was added while mixing in order to achieve a final SDS concentration of 2.0% (w/v). The suspension was heated from room temperature to approximately 93° C. over a period of 45 minutes with stirring in a water bath heated to about 95° C. This SDS (#1) suspension was centrifuged for 20 minutes at 7,500 rpm in a GSA rotor using a Sorvall RC5B centrifuge (centrifugal force=9,179×gravity) at 4° C. The SDS (#1) supernatant was removed and discarded.

The total protein and polymer product concentrations in both the supernatants and pellets were determined after each centrifugation step, by Lowry and immunological dot blot analyses, respectively. The protein purity of the final pellet was determined by amino acid composition. Results were as shown in Table 3.

Example 6

The protein polymer, SLP3-C, was recovered and purified from 125 grams of frozen cell paste of E. coli strain PPT$_{0105}$ (HB101) containing the gene encoding SLP3-C. The cell paste was suspended to a volume of 500 ml with 50 mM Tris buffer, pH-8.0 and allowed to thaw to room temperature. The suspension was homogenized to yield a homogeneous cell suspension. The suspension was subjected to cellular disruption using a Manton-Gaulin (MG15) press at 8,000 psi for 3 successive passes. The cell lysate was centrifuged for a 3 minute plateau at 5,000 rpm in a GSA rotor using a Sorvall RC5B centrifuge (centrifugal force=4,080×gravity) at 4° C. The cell lysate supernatant was removed and discarded.

The cell lysate pellet was resuspended to a volume of 0.45 liter with water. The suspension was homogenized until a homogeneous slurry was obtained. 50 ml of a 20% (w/v) solution of sodium dodecyl sulphate (SDS) (technical grade, Sigma) was added while mixing in order to achieve a final SDS concentration of 2.0% (w/v). The suspension was heated from room temperature to approximately 93° C. over a period of 40 minutes with stirring in a water bath heated to about 95° C. This SDS (#1) suspension was centrifuged for 20 minutes at 7,500 rpm in a GSA rotor using a Sorvall RC5B centrifuge (centrifugal force=9,179×gravity) at 4° C. The SDS (#1) supernatant was removed and discarded.

The total protein and polymer product concentrations in both the supernatants and pellets were determined after each centrifugation step, by Lowry and immunological dot blot analyses, respectively. The protein purity of the final pellet was determined by amino acid composition. Results were as shown in Table 3.

TABLE 3

Summary of Experimental Results

| Example | Polymer | Scale | Biomass | | CELL LYSATE % Protein | % SLP | LYSATE CENTRIFUGATION | | | | SDS #1 | | | |
|---|---|---|---|---|---|---|---|---|---|---|---|---|---|---|
| | | | | | | | % Protein | Super % SLP | Pellet % Protein | % SLP | % Protein | Super % SLP | Pellet % Protein | % SLP |
| 1 | SLP3 | Lab | Frozen paste | | 100.00 | 100.00 | 20.69 | 0.00 | 79.31 | 100.00 | 56.01 | 1.90 | 43.99 | 98.10 |
| 2 | SLP3 | Lab | Fresh paste | | 100.00 | 100.00 | 66.57 | 5.86 | 33.43 | 94.14 | 70.12 | 6.83 | 29.88 | 93.17 |
| 3 | SLP4 | Pilot | Frozen slurry | A | 100.00 | 100.00 | 63.00 | 5.06 | 37.00 | 94.96 | 77.22 | 9.68 | 22.78 | 90.42 |
| | | | | B COMS | 100.00 | 100.00 | 62.66 | 2.53 | 37.34 | 97.47 | 64.82 | 3.71 | 36.18 | 94.40 |
| 4 | SLP4 | Lab | Frozen slurry | | 100.00 | 100.00 | 50.44 | 0.00 | 49.56 | 100.00 | 30.68 | 0.10 | 69.32 | 99.90 |
| 5 | SLP3-F | Lab | Frozen paste | | 100.00 | 100.00 | 74.68 | 5.68 | 25.32 | 94.32 | 80.49 | 11.31 | 19.61 | 88.69 |
| 6 | SLP3-C | Lab | Frozen paste | | 100.00 | 100.00 | 82.56 | 69.99 | 17.64 | 30.01 | 83.27 | 55.44 | 18.73 | 44.58 |

| Example (Conc) | SDS #2 | | | | Water Wash #1 | | | | Water Wash #2 | | | | % Purity | |
|---|---|---|---|---|---|---|---|---|---|---|---|---|---|---|
| | % Protein | Super % SLP | Pellet % Protein | % SLP | % Protein | Super % SLP | Pellet % Protein | % SLP | % Protein | Super % SLP | Pellet % Protein | % SLP | Protein | Absolute |
| 1 | 41.10 | 2.13 | 58.90 | 97.87 | 4.59 | 2.31 | 95.41 | 97.69 | 2.61 | 5.89 | 97.39 | 94.11 | 100.00 | 86.77 |
| 2 | | | | | | | | | | | | | 66.67 | NA |
| 3 | 8.37 | 4.31 | 91.63 | 96.69 | 6.04 | 0.79 | 93.94 | 99.21 | 11.61 | 11.61 | 88.39 | 88.39 | 96.40 | 82.80 |
| 4 | 17.58 | | 82.42 | | 2.58 | | 97.42 | | 1.90 | | 98.10 | | 94.80 | NA |
| 5 | | | | | | | | | | | | | 68.40 | NA |
| 6 | | | | | | | | | | | | | 61.45 | NA |

It is evident from the above results, that the subject method provides a simple and efficient procedure for purifying intractable polymers insoluble in conventional solvent, while retaining their desirable physical characteristics. The method employs simple economic reagents and readily available equipment. High purity levels may be achieved.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

---

What is claimed is:

1. A method of purification of substantially insoluble protein polymers, said polymers being characterized by being prepared by recombinant techniques, having long stretches of repeating units of silk fibroin and sufficient stretches of the repeating units so that the polymers have the structural order of silk, said method comprising:
   treating and lysing cells to provide lysate comprising said protein polymers in insoluble form;
   suspending the disrupted cells from said lysate in an aqueous medium;
   separating high molecular weight insoluble material from the suspension;
   extracting said separated high molecular weight insoluble material at a temperature in the range of about 60° to 100° C. with an aqueous detergent solution; and
   isolating the purified protein polymer.

2. A method according to claim 1, wherein lysing comprises mechanical disruption and said separating comprises centrifugation.

3. A method according to claim 1, wherein said extracting is performed at a temperature of at least about 80° C. and said detergent solution is sodium dodecylsulfate.

4. A method according to claim 1, wherein said isolating is by centrifugation.

5. A method of purification of substantially insoluble protein polymers, said polymers being characterized by being prepared by recombinant techniques, having long stretches of silk fibroin repeating units and having sufficient stretches of the repeating units so that the polymers have the structural order of silk, said method comprising:
   treating and lysing cells comprising said protein polymers by mechanical disruption to provide lysate comprising said protein polymers in insoluble form;
   separating high molecular weight insoluble material from said lysate by means of centrifugation;
   extracting said separated high molecular weight insoluble material at a temperature in the range of about 80° to 100° C. with an aqueous anionic sulfuric acid based detergent solution, said detergent being present in from about 1 to 3% w/v; and
   isolating the purified protein polymer by centrifugation.

6. A method according to claim 5, wherein said aqueous anionic sulfuric acid based detergent solution is 1.5 to 3% w/v.

* * * * *